US006992075B2

(12) United States Patent
Hill et al.

(10) Patent No.: US 6,992,075 B2
(45) Date of Patent: Jan. 31, 2006

(54) C(14) ESTROGENIC COMPOUNDS (75) Inventors: Edward N. Hill, Wilmington, NC (US); Thomas W. Leonard, Wilmington, NC (US); Robert R. Whittle, Wilmington, NC (US)

(73) Assignee: Barr Laboratories, Inc., Woodcliffe Lake, NJ (US)

( * ) Notice: Subject to any disclaimer, the term of this patent is extended or adjusted under 35 U.S.C. 154(b) by 358 days.

(21) Appl. No.: 10/407,509

(22) Filed: Apr. 4, 2003

(65) Prior Publication Data
US 2004/0198670 A1  Oct. 7, 2004

(51) Int. Cl.
*A61K 31/56* (2006.01)
*C07J 1/00* (2006.01)

(52) U.S. Cl. .................. 514/179; 514/182; 552/618
(58) Field of Classification Search ............... 552/618; 514/179, 182
See application file for complete search history.

(56) References Cited

U.S. PATENT DOCUMENTS

| | | | |
|---|---|---|---|
| 3,230,142 A | 1/1966 | Spero | 167/55 |
| 3,487,152 A | 12/1969 | Carstensen et al. | 424/240 |
| 3,502,772 A | 3/1970 | Ijzerman | 424/239 |
| 3,568,828 A | 3/1971 | Lerner | 206/42 |
| 3,591,688 A | 7/1971 | Jones et al. | 424/239 |
| 3,639,600 A | 2/1972 | Hnedrix | 424/242 |
| 3,733,407 A | 5/1973 | Segre | 424/239 |
| 3,795,734 A | 3/1974 | Rochefort | 424/238 |
| 3,813,418 A | 5/1974 | Hofmeister et al. | 260/397.4 |
| 3,836,651 A | 9/1974 | Rudel et al. | 424/239 |
| 3,932,635 A | 1/1976 | Segre | 424/239 |
| 3,939,264 A | 2/1976 | Lachnit-Fixson | 424/239 |
| 3,942,641 A | 3/1976 | Segre | 206/534 |
| 3,957,982 A | 5/1976 | Lachnit-Fixson et al. | 424/238 |
| 3,969,502 A | 7/1976 | Lachnit-Fixson | 424/239 |
| 4,027,019 A | 5/1977 | Shroff | 424/238 |
| 4,066,757 A | 1/1978 | Pasquale | 424/243 |
| 4,071,623 A | 1/1978 | van der Vies | 424/238 |
| 4,145,416 A | 3/1979 | Lachnit-Fixson et al. | 424/238 |
| 4,147,783 A | 4/1979 | van der Vies | 424/243 |
| 4,154,820 A | 5/1979 | Simoons | 424/175 |
| 4,210,644 A | 7/1980 | Ewing et al. | 424/239 |
| 4,259,325 A | 3/1981 | Prezewowsky et al. | 424/238 |
| 4,291,028 A | 9/1981 | Vorys | 424/238 |
| 4,292,315 A | 9/1981 | Vorys | 424/240 |
| 4,315,925 A | 2/1982 | Hussain et al. | 424/239 |
| 4,327,725 A | 5/1982 | Cortese et al. | 128/260 |
| 4,378,356 A | 3/1983 | De Jager | 424/238 |
| 4,383,993 A | 5/1983 | Hussain et al. | 424/239 |
| 4,390,531 A | 6/1983 | Edgren | 424/239 |
| 4,425,339 A | 1/1984 | Pitchford | 424/239 |
| 4,512,986 A | 4/1985 | Reel et al. | 514/170 |
| 4,530,839 A | 7/1985 | Pasquale | 514/171 |
| 4,544,554 A | 10/1985 | Pasquale | 514/170 |
| 4,616,006 A | 10/1986 | Pasquale | 514/170 |
| 4,621,079 A | 11/1986 | Lachnit-Fixson et al. | 514/170 |
| 4,628,051 A | 12/1986 | Pasquale | 514/170 |
| 4,738,957 A | 4/1988 | Laurent et al. | 514/182 |
| 4,756,907 A | 7/1988 | Beck et al. | 424/85 |
| 4,762,717 A | 8/1988 | Crowley, Jr. | 424/425 |
| 4,764,378 A | 8/1988 | Keith et al. | 424/435 |
| 4,783,337 A | 11/1988 | Wong et al. | 424/468 |
| 4,816,257 A | 3/1989 | Buster et al. | 424/430 |
| 4,816,258 A | 3/1989 | Nedberge et al. | 424/448 |
| 4,826,831 A | 5/1989 | Plunkett et al. | 514/170 |
| 4,855,305 A | 8/1989 | Cohen | 514/171 |
| 4,900,734 A | 2/1990 | Maxson et al. | 514/171 |
| 4,914,089 A | 4/1990 | Tax | 514/170 |
| 4,921,843 A | 5/1990 | Pasquale | 514/170 |
| 4,962,098 A | 10/1990 | Boissonneault | 514/170 |
| 4,977,147 A | 12/1990 | Jungblut et al. | 514/171 |
| 5,006,345 A | 4/1991 | Lang | 424/467 |
| 5,010,070 A | 4/1991 | Boissonneault | 514/171 |
| 5,043,331 A | 8/1991 | Hirvonen et al. | 514/170 |
| 5,089,482 A | 2/1992 | Hermens et al. | 514/58 |
| 5,098,714 A | 3/1992 | Wright et al. | 424/473 |
| 5,108,995 A | 4/1992 | Casper | 514/170 |
| 5,130,137 A | 7/1992 | Crowley, Jr. | 424/422 |
| 5,183,814 A | 2/1993 | Dukes | 514/171 |
| 5,200,197 A | 4/1993 | Wright et al. | 424/473 |
| 5,208,225 A | 5/1993 | Boissonneault et al. | 514/178 |
| 5,210,081 A | 5/1993 | Raveendranath et al. | 514/179 |
| 5,262,408 A | 11/1993 | Bergink | 514/182 |
| 5,276,022 A | 1/1994 | Casper | 514/170 |
| 5,280,023 A | 1/1994 | Ehrlich et al. | 514/177 |
| 5,288,717 A | 2/1994 | Raveendranath et al. | 514/179 |
| 5,362,720 A | 11/1994 | Labrie | 514/169 |
| 5,382,573 A | 1/1995 | Casper | 514/170 |
| 5,418,228 A | 5/1995 | Bennink | 514/182 |
| 5,434,146 A | 7/1995 | Labrie et al. | 514/169 |
| 5,464,871 A | 11/1995 | Kun et al. | 514/617 |
| 5,510,342 A | 4/1996 | Washburn et al. | 514/179 |
| 5,541,172 A | 7/1996 | Labrie et al. | 514/169 |
| 5,545,634 A | 8/1996 | Labrie | 514/169 |

(Continued)

OTHER PUBLICATIONS

Andreolini, et al., *Estrogen Conjugates in Late-Pregnancy Fluids: Extraction and Group Separation by a Graphitized Carbon Black Cartridge and Quantification by High-Performance Liquid Chromatography*, Anal. Chem. 59:1720-1725 (1987).

(Continued)

*Primary Examiner*—Barbara P. Badio
(74) *Attorney, Agent, or Firm*—Myers Bigel Sibley & Sajovec (57) ABSTRACT The present invention relates to novel estrogenic compounds. The present invention also relates to methods of treating estrogen deprivation in a subject comprising administering novel estrogenic compounds. Additionally, the present invention relates to methods of synthesizing novel estrogenic compounds.

13 Claims, 7 Drawing Sheets

U.S. PATENT DOCUMENTS

| | | | |
|---|---|---|---|
| 5,547,948 A | 8/1996 | Barcomb | 514/170 |
| 5,567,695 A | 10/1996 | Labrie | 514/169 |
| 5,629,303 A | 5/1997 | Labrie et al. | 514/169 |
| 5,654,011 A | 8/1997 | Jackson et al. | 424/635 |
| 5,753,639 A | 5/1998 | Labrie | 514/169 |
| 5,759,576 A | 6/1998 | Barcomb | 424/479 |
| 5,759,577 A | 6/1998 | Barcomb | 424/479 |
| 5,807,586 A | 9/1998 | Jackson et al. | 424/630 |
| 5,846,960 A | 12/1998 | Labrie | 514/169 |
| 5,861,387 A | 1/1999 | Labrie et al. | 514/169 |
| 5,861,431 A | 1/1999 | Hildebrand et al. | 514/557 |
| 5,908,638 A | 6/1999 | Huber et al. | 424/465 |
| RE36,247 E | 7/1999 | Plunkett et al. | 514/170 |
| 5,998,639 A | 12/1999 | Raijmakers et al. | 552/625 |
| 6,040,333 A | 3/2000 | Jackson | 514/456 |

OTHER PUBLICATIONS

Center for Drug Evaluation and Research (CDER), Guidance for Industry, Draft Guidance, *Conjugated Estrogens. USP—LC-MS Method for Both Qualitative Chemical Characterization and Documentation of Qualitative Pharmaceutical Equivalence*, Mar. 2000, <http://www.fda.gov/cder/guidance/index.htm>.

*Conjugated Estrogens*. The United States Pharmacopeia (USP), published by United States Pharmacopeial Convention, Inc., pp. 627-629 (2000).

FDA Backgrounder on Conjugated Estrogens, May 5, 1997, <http://www.fda.gov/cder/cebackground.htm>.

FDA Statement on generic Premarin, HHS News Press Release, P97-12, May 5, 1997, <http://www.fda.gov/cder/cepressrelease.htm>.

Fujino, et al., *3-(Difluoro-1,3,5-trianinyl)-1-(ethylthio)-2-n-propylbenz[f]isoindole as a Fluorescence Derivation Reagent for Estrogens in High-Performance Liquid Chromatography*, Chem. Pharm. Bull., 37(7): 1939-1940 (1989).

International Search Report corresponding to PCT/US 01/07544; mailed on Aug. 6, 2001.

Ishida, et al., *Determination of Oestrogens in Pregnancy Urine by High-Performance Liquid Chromatography with Fluorescence Detection*, Journal of Chromatography, 431: 249-257 (1988).

Letter from Yana Ruth Mille, Chief, Compendial Operations Staff, HFD-354, Office of Pharmaceutical Science, Center for Drug Evaluation & Research to Joseph G. Valentino, J.D., Senior Vice President and General Counsel, The United States Pharmacopeial Convention, Inc. (Mar. 8, 2000) (REF: 3-00-001-O).

Letter from Yana Ruth Mille, Chief, Compendial Operations Staff, HFD-354, Office of Pharmaceutical Science, Center for Drug Evaluation & Research to Joseph G. Valentino, J.D., Senior Vice President and General Counsel, The United States Pharmacopeial Convention, Inc. (Mar. 8, 2000) (REF: 3-00-002-O).

Memorandum from Janet Woodcock, M.D., Director, Center for Drug Evaluation & Research to Douglas L. Sporn, Director, Office of Generic Drugs, regarding Approvability of a Synthetic Generic Version of Premarin (May 5, 1997).

NDA 20-992 Cenestin™ (synthetic conjugated estrogens, A) Tablets Physicians Package Insert, pp. 1-10 (1999).

NDA 20-992 Cenestin™ (synthetic conjugated estrogens, A) Tablets Patient Package Insert, pp. 11-13 (1999).

New Drug Approval for Cenestin, Synthetic Conjugated Estrogens, A: Mar. 24, 1999, *Questions and Answers*, <http://www.fda.gov/cder/news/cenestin/qa.htm>.

Novakovic, et al., *High-Performance Liquid Chromatographic Dtermination of Equine Estrogens with Ultraviolet Absorbance and Electrochemical Detection*, Journal of Chromatography A, 678: 359-363 (1994).

Physician's Desk Reference, 53: 3367-3379 (1999).

Rzheznikov, V. M. et al., "Synthesis and Biological Activity of Estrone 8-iso- and D-homoanalogs Oxidized for Rings B and C," *Database Chemabs 'Online!*, Journal of Chromatography A, 678: 359-363 (1994).

Sakac, Marija N. et al., "Synthesis of New Steroidal N-butyl-N-methyl-undecanamide Derivatives," *Database Chemabs 'Online!*, Database accession No. 133:335378 XP002171995, Zb. Matice Srp. Prir. Nauke 96: 5-9 (1999).

Sakac, Marijan N. et al., "Chemical Behavior of 3, 17.beta.-dipropionoxy-9.alpha.-hydroxyestra-1,3,5(10)-trien-6-one," *Database Chemabs 'Online!*, Database accession No. 128: 180573 XP002171996, J. Serb. Chem. Soc., 63(1): 21-24 (1998).

Synthetic Generic Conjugated Estrogens: Timeline, May 5, 1997, <http://www.fda.gov/cder/news/cetimeline.htm>.

Takadate, et al., *A Convenient Derivatization with Anion Exchange Resin Catalysts for High-Performance Liquid Chromatographic Analysis. I. Derivatization of Estrogens with Dansyl Chloride*, Chem. Pharm. Bull., 33(11): 5092-5095 (1985).

Townsend, et al., *High-Performance Liquid Chromatographic Determination of Conjugated Estrogens in Tablets*, Journal Chromatography, 450: 414-419 (1988).

Wiese, Thomas et al., "Induction of the Estrogen Specific Mitogenic Response of MCF-7 Cells by Selected Analogues of Estradiol-17β: A 3D Study," *Journal of Medicinal Chemistry*, 40(22): 3659-3669 (1997).

Yang et al., "The Hydroxylation and Amidation of Equilenin Acetate Catalyzed by Chloro[5,10,15,20-tetrakis (pentafluorophenyl)porphyrinato]manganese(III)," *Chem. Commun.*, 7: 531-532 (2000).

Yang, Jerry et al., "Regioselective Oxidations of Equilenin Derivatives Catalyzed by a Rhodium(III) Porphyrin Complex-Contrast with the Manganese(III) Porphyrin," *Tetrahedron Letters*, 41(42): 8063-8067 (2000).

C(14) ESTROGENIC COMPOUNDS

FIELD OF THE INVENTION

The present invention relates to the field of estrogenic compounds.

BACKGROUND OF THE INVENTION

Women, particularly menopausal and post-menopausal women, often experience a wide variety of conditions and disorders attributable to estrogen deprivation. Estrogen deprivation is often associated with the loss of ovarian function. This may result in hot flashes, dryness of the vagina, discomfort during intercourse, loss of bone mass, increased heart disease and the like.

Providing dosages of estrogen is an effective agent for the control or prevention of such conditions, particularly in controlling or preventing hot flashes and vaginal atrophy, along with retarding or preventing osteoporosis. Estrogen is typically administered alone or in combination with a progestin.

As detailed in U.S. Pat. No. Re. 36,247 to Plunkett et al., estrogen alone, given in small doses, on a continuous basis, is effective in most patients for the control of the above symptoms and problems associated therewith. However, although the vast majority of women taking continuous low-dose estrogen will not have bleeding for many months or even years, there is a distinct risk posed by this routine of developing "hyperplasia of the endometrium". This phrase refers to an overstimulation of the lining of the uterus which can become pre-malignant, coupled with the possibility that the patient may eventually develop cancer of the uterine lining even under such a low-dose regimen (Gusberg et al., Obstetrics and Gynaecology, 17, 397–412, 1961).

Estrogen alone may be given in cycles, usually 21–25 days on treatment and 5–7 days off treatment. When small doses of estrogen are required to control the symptoms generally only about 10% of women experience withdrawal bleeding between the cycles of actual treatment. However, the risk of developing endometrial hyperplasia and the increased relative risk of developing cancer of the uterus may still be present with this method (Research on the Menopause: Report of a W.H.O. Scientific Group, 53–68, 1981).

The addition of a progestin for the last 7–10 days of each estrogen cycle helps to reduce concerns about developing endometrial hyperplasia and/or also reduces the risk of developing endometrial carcinoma below that of the untreated general population. However, withdrawal bleeding may occur regularly in this routine and this is generally not preferable to most older women (Whitehead, Am. J. Obs/Gyn., 142,6, 791–795, 1982).

Another routine for estrogen administration may involve a formulation such as those found in birth control pills which contain relatively small doses of estrogen over the full 20–21 day treatment cycle, plus very substantial doses of potent progestins over the same period of time. This routine, of course not only produces withdrawal bleeding on each cycle, but is also generally unacceptable because such formulations have been shown to carry an increased risk of developing arterial complications, such as stroke or myocardial infarction in older women about the age of 35–40. This is especially true if the individual is a smoker of cigarettes (Plunkett, Am. J. Obs/Gyn. 142,6, 747–751, 1982). Thus, there remains a need for novel isolated estrogenic compounds.

SUMMARY OF THE INVENTION

The present invention relates to novel estrogenic compounds comprising the formula:

wherein $R_1$ is selected from the group consisting peroxy, hydroxy, halogen, and thiol, or a pharmaceutically acceptable salt thereof, $R_2$ is selected from the group of glucuronide, sulfate, phosphate and pyrophosphate, and $R_3$ is selected from the group consisting of hydroxy, ester, and ketone. The present invention also relates to methods of treating estrogen deprivation in a subject comprising administering the novel estrogenic compounds. Additionally, the present invention relates to methods of synthesizing novel estrogenic compounds.

BRIEF DESCRIPTION OF THE FIGURES OF THE INVENTION

DETAILED DESCRIPTION OF THE INVENTION

In one aspect, the invention relates to a method of synthesizing an estrogenic composition. For the purposes of the invention, the estrogenic composition may encompass various compounds. Preferably, the estrogenic composition includes at least one conjugated estrogen. The conjugates may be various conjugates understood by those skilled in the art, including, but not limited to, sulfate and glucuronide. The most preferred estrogen conjugates are estrogen sulfates. The estrogenic compounds may also be present as salts of estrogen conjugates. The salts may be various salts understood by those skilled in the art, including, but not limited to, sodium salts, calcium salts, magnesium salts, lithium salts, and piperazine salts. The most preferred salts are sodium salts.

The present invention may act as an agonist, partial agonist or antagonist. The term "antagonist" may be generally defined as a substance that tends to nullify the action of another, i.e., as a drug that binds to a cell receptor without eliciting a biological response. The term "agonist" is known in the art, and, as used herein, generally refers to a drug that has affinity for and stimulates physiologic activity at cell receptors normally stimulated by naturally occurring substances, thus triggering a biochemical response. A "partial agonist" may itself cause agonist effects, but because they can displace through competitive action a full agonist from its receptor, the net effect is a reduction in drug effect. As a result, a partial agonist, depending on circumstance, can act as either in agonist or an antagonist.

In one embodiment of the present invention, the estrogenic composition of the invention may include at least one additional pharmaceutically active ingredient, including, but are not limited to, androgens, progestins, calcium salts, and vitamin D and its derivatives such as calcitriol, and mixtures and blends thereof.

Pharmaceutically acceptable salts, solvates, hydrates, and polymorphs may be formed of any of the active ingredients employed in the estrogenic composition of the invention. The invention also encompasses embodiments in which the composition defined herein is included in various quantities in combination with known pharmaceutically accepted formulations. For example, the composition of matter of the invention may be incorporated into various known estrogen-containing drug products such as, Premarin® made commercially available by Wyeth-Ayerst Laboratories of Philadelphia, PA. The composition of matter of the invention may also be employed as part of a continuous estrogen-progestogen therapy regimen such as that described by U.S. Pat. No. Re. 36,247 to Plunkett et al. and is present commercially as Prempro® and Premphase® made available by Wyeth-Ayerst Laboratories, the disclosure of which is incorporated herein by reference in its entirety.

Various estrogen-containing samples may be evaluated by LC-MS and accurate mass analyses and UV spectra. In general, certain peaks are first characterized by mass spectrometric response (nominal mass) during LC-MS. Such peaks are then analyzed by direct infusion, and high-resolution electrospray mass spectrometry in order to attempt to obtain accurate mass measurements.

In one aspect of the present invention, a compound represented by Formula I is provided.

wherein $R_1$ is selected from the group consisting of peroxy, hydroxy, halogen, ester, glucuronide, sulfate, phosphate, pyrophosphate and thiol groups, $R_2$ is selected from the group of glucuronide, sulfate, phosphate and pyrophosphate, and $R_3$ is selected from the group consisting of hydroxy, ester, and ketone. The compound represented by Formula I is present in chemically pure form, (i.e., greater than about 90% pure). The compound represented by Formula I is preferably greater than about 95% pure, and is most preferably greater than about 99% pure. The base compound, wherein $R_1$ is hydrogen and $R_2$ is sulfate, has the chemical compound $C_{18}H_{19}NaO_5S$, a mass of 370.41 amu and is known as $\Delta^{8,9}$-Dehydroestrone Sodium Sulfate.

A preferred compound is illustrated in Formula II (referred to herein as Compound "C"):

wherein the above compound has the name 14-hydroxy-$\Delta^{8,9}$-Dehydroestrone Sodium Sulfate with the formula $C_{18}H_{19}NaO_6S$ and has a mass of approximately 386.41 amu.

Another preferred compound is illustrated in Formula IV (referred to herein as Compound "E"):

wherein the above compound has the name 14-hydroperoxy-$\Delta^{8,9}$-Dehydroestrone Sodium Sulfate with the formula $C_{18}H_{19}NaO_7S$ and has a mass of approximately 402.41 amu. Compounds of the present invention may be present in a conjugated form, wherein the most preferred conjugate is sulfate.

Compounds of the present invention may also be present as various pharmaceutically acceptable salts including salts of the conjugated compound. The salts may be various salts understood by those skilled in the art, including, but not limited to, sodium salts, calcium salts, magnesium salts, lithium salts, and amine salts such as piperazine salts. The most preferred salts are sodium salts.

Examples of estrogenic compounds and compositions are set forth in U.S. patent application Ser. No. 09/524,132 filed on Mar. 10, 2000, which is commonly assigned to the assignee of the present invention, the disclosure of which is incorporated by reference herein in its entirety. Suitable estrogenic compounds include estrone, 17α-estradiol, 17β-estradiol, equilin, 17α-dihydroequilin, 17β-dihydroequilin, equilenin, 17α-dihydroequilenin, 17β-dihydroequilenin, $\Delta^{8,9}$-dehydroestrone, 17-$\Delta^{8,9}$-dehydroestradiol, 17-$\Delta^{8,9}$-dehydroestradio ethinyl estradiol, estradiol valerate, 6-OH equilenin, 6-OH 17-α dihydroequilenin, 6-OH 17-β dihydroequilenin, and mixtures, conjugates and salts thereof, and the estrogen ketones and their corresponding 17α- and 17β-hydroxy derivatives. The estrogenic compounds may also be present as conjugated estrogens. The conjugates may be various conjugates understood by those skilled in the art, including, but not limited to, sulfate and glucuronide. The most preferred estrogen conjugates are estrogen sulfates. The estrogenic compounds may also be present estrogen conjugates. In one embodiment, the estrogenic compounds are present as salts of estrogen conjugates. The salts may be various salts understood by those skilled in the art, including, but not limited to, sodium salts, calcium salts, magnesium salts, lithium salts, and piperazine salts. The most preferred salts are sodium salts. The estrogenic compounds can be derived from natural and synthetic sources.

Examples of androgens include, without limitation, methyltestosterone; fluoxymesterone; oxandrolone; oxymetholone; stanozolol; 7α-methyl-19-nortestosterone; testosterone; testosterone cypionate; testosterone enanthate; testosterone propionate; danazol; 5α-androstan-3α-ol-16-one; 5α-androstan-3β,16β-diol; 5α-androstan-3β,16α-diol; and 5α-androstan-3β,17α-diol. Examples of progestins are set forth in U.S. Pat. No. Re. 36,247 to Plunkett et al., the disclosure of which is incorporated herein in its entirety. Examples include, but are not limited to, desogestrel; dydrogesterone; ethynodiol diacetate; medroxyprogesterone acetate; levonorgestrel; medroxyprogesterone acetate; hydroxyprogesterone caproate; norethindrone; norethindrone acetate; norethynodrel; allylestrenol; 19-nortestosterone; lynoestrenol; quingestanol acetate; medrogestone; norgestrienone; dimethisterone; ethisterone; cyproterone acetate; chlormadinone acetate; megestrol acetate; norgestimate; norgestrel; desogestrel; trimegestone; gestodene; nomegestrel acetate; progesterone; 5α-pregnan-3β,20α-diol sulfate; 5α-pregnan-3β,20β-diol sulfate; 5α-pregnan-3β-ol-20-one; 16,5α-pregnen-3β-ol-20-one; and 4-pregnen-20β-ol-3-one-20-sulfate, and pharmaceutically acceptable esters and salts thereof, and combinations of any of the foregoing.

Suitable vasodilation compounds include alpha andrenergic antagonists. Exemplary α-adrenergic compounds include phentolamine, phenoxybenzalamine, tolazoline, doxazosin, dibenamine, prazosin, prazosin hydrochloride, phenoxybenzamine and the like. Preferably, phentolamine is used and can form pharmaceutically acceptable salts with organic and inorganic acids, as described, for example, in U.S. Pat. No. 6,001,845 to Estok, the disclosure of which is incorporated herein by reference in its entirety. Preferably phentolamine mesylate or phentolamine hydrochloride is used. Other vasodilation compounds include phosphodiesterase type 5 inhibitors (e.g., suldenafil), prostaglandin E compounds (e.g., alprostodil), thymoxamine, bromocriptine, yohimbine, paperverine, apomorphine, organic nitrates, imipramine, verapamil, naftidrofuryl, and isoxsuprine. Combinations of the various vasodilation compounds may be used.

Examples of progestins are set forth in U.S. Pat. No. Re. 36,247 to Plunkett et al., the disclosure of which is incorporated herein by reference in its entirety. Suitable progestin compounds include desogestrel, dydrogesterone, ethynodiol diacetate, medroxyprogesterone, levonorgestrel, medroxyprogesterone acetate, hydroxyprogesterone caproate, norethindrone, norethindrone acetate, norethynodrel, allylestrenol, 19-nortestosterone, lynoestrenol, quingestanol acetate, medrogestone, norgestrienone, dimethisterone, ethisterone, cyproterone acetate, chlormadinone acetate, megestrol acetate, norgestimate, norgestrel, desogestrel, trimegestone, gestodene, nomegestrol acetate, progesterone, 5α-pregnan-3β,20α-diol sulfate, 5α-pregnan-3β,20β-diol sulfate, 5α-pregnan-3β-ol-20-one, 16, 5α-pregnen-3β-ol-20-one, 4-pregnen-20β-ol-3-one-20-sulfate and mixtures thereof.

Calcium salts may include, without limitation, organic acid salts of calcium such as calcium citrate, calcium lactate, calcium fumurate, calcium acetate, and calcium glycerophosphate, as well as inorganic salts such as calcium chloride, calcium phosphate, calcium sulphate, and calcium nitrate.

The present invention also encompasses pharmaceutically acceptable drug products comprising a composition of matter of the present invention and at least one pharmaceutically acceptable carrier, diluent, or excipient, the selection of which are known to the skilled artisan. The drug product formulations can be in various forms such as, for example, tablets; effervescent tablets; pills; powders; elixirs; suspensions; emulsions; solutions; syrups; soft and hard gelatin capsules; transdermal patches; topical gels, creams and the like; suppositories; sterile injectable solutions; and sterile packaged powders, sublingual tablets, buccal tablets, and buccal adhesive systems.

In certain embodiments, the drug product is present in a solid pharmaceutical composition that may be suitable for oral administration. A solid estrogenic composition according to the present invention may be formed and may be mixed with an excipient, diluted by an excipient or enclosed within such a carrier which can be in the form of a capsule, sachet, tablet, paper, or other container. When the excipient serves as a diluent, it may be a solid, semi-solid, or liquid material which acts as a vehicle, carrier, or medium for the composition of matter.

Various suitable excipients will be understood by those skilled in the art and may be found in the *National Formulary* 19, pages 2404–2406 (2000), the disclosure of pages 2404 to 2406 being incorporated herein in their entirety. Examples of suitable excipients include, but are not limited to, starches, gum arabic, calcium silicate, microcrystalline cellulose, methacrylates, shellac, polyvinylpyrrolidone, cellulose, water, syrup, and methylcellulose. The drug product formulations can additionally include lubricating agents such as, talc, magnesium stearate and mineral oil; wetting agents; emulsifying agents; suspending agents; preserving agents such as methyl- and propyl hydroxybenzoates; sweetening agents; and/or flavoring agents. Polyols, buffers, and inert fillers may also be used. Examples of polyols include, but are not limited to, mannitol, sorbitol, xylitol, sucrose, maltose, glucose, lactose, dextrose, and the like. Suitable buffers encompass, but are not limited to, phosphate, citrate, tartarate, succinate, and the like. Other inert fillers which may be used encompass those which are known in the art and are useful in the manufacture of various dosage forms. If desired, the solid formulations may include other components such as bulking agents and/or granulating agents, and the like. The drug products of the invention may be formulated so as to provide quick, sustained, or delayed release of the active ingredient after administration to the patient by employing procedures well known in the art.

To form dosage units for oral administration, the estrogenic composition of the present invention may be mixed with a solid, pulverant carrier such as, for example, lactose, saccharose, sorbitol, mannitol, starch, amylopectin, cellulose derivatives or gelatin, as well as with an antifriction agent such as, for example, magnesium stearate, calcium stearate, and polyethylene glycol waxes. The mixture may then be pressed into tablets. Tablets for oral use are typically prepared in the following manner, although other techniques may be employed. The solid substances are ground or sieved to a desired particle size, and the binding agent is homogenized and suspended in a suitable solvent. The active ingredient and auxiliary agents are mixed with the binding agent solution. The resulting mixture is moistened to form a uniform suspension. The moistening typically causes the particles to aggregate slightly, and the resulting mass is pressed through a stainless steel sieve having a desired size. The layers of the mixture are then dried in controlled drying units for a determined length of time to achieve a desired particle size and consistency. The granules of the dried mixture may then be sieved to remove any powder. To this mixture, disintegrating, antifriction, and anti-adhesive agents may be added. Finally, the mixture is pressed into tablets using a machine with the appropriate punches and dies to obtain the desired tablet size. The operating parameters of the machine may be selected by the skilled artisan.

If coated tablets are desired, the above prepared core may be coated with a concentrated solution of sugar, which may contain gum arabic, gelatin, talc, titanium dioxide, or with a lacquer dissolved in volatile organic solvent or mixture of solvents. To this coating various dyes may be added in order to distinguish among tablets with different active compounds or with different amounts of the active compound present. In a particular embodiment, the active ingredient may be present in a core surrounded by one or more layers including an enteric coating layers.

Soft gelatin capsules may be prepared in which capsules contain a mixture of the active ingredient and vegetable oil. Hard gelatin capsules may contain granules of the active ingredient in combination with a solid, pulverulent carrier, such as, for example, lactose, saccharose, sorbitol, mannitol, potato starch, corn starch, amylopectin, cellulose derivatives, or gelatin.

In one preferred embodiment, the formulation is in the form of orally-administered tablets which contain the estrogenic composition of the present invention as set forth herein along with the following inactive ingredients: calcium phosphate tribasic, calcium sulfate, carnauba wax, cellulose, glyceryl monooleate, lactose, magnesium stearate, methylcellulose, pharmaceutical glaze, polyethylene glycol, stearic acid, sucrose, and titanium dioxide. Such ingredients may be present in amounts similar to those present in Premarin® (conjugated estrogens tablets, USP) made commercially available by Wyeth-Ayerst Laboratories of Philadelphia, Pa. Tablets employing the active ingredients of the invention may contain excipients similar to those contained in the 0.3 mg., 0.625 mg., and 1.25 mg tablets of Premarin® (conjugated estrogens tablets, USP).

Liquid preparations for oral administration may be prepared in the form of syrups or suspensions, e.g., solutions containing an active ingredient, sugar, and a mixture of ethanol, water, glycerol, and propylene glycol. If desired, such liquid preparations may contain coloring agents, flavoring agents, and saccharin. Thickening agents such as carboxymethylcellulose may also be used.

In the event that the above formulations are to be used for parenteral administration, such a formulation may comprise sterile aqueous injection solutions, non-aqueous injection solutions, or both comprising the estrogenic composition of the present invention. When aqueous injection solutions are prepared, the estrogenic composition may be present as a water soluble pharmaceutically acceptable salt. Parenteral preparations may contain anti-oxidants, buffers, bacteriostats, and solutes which render the formulation isotonic with the blood of the intended recipient. Aqueous and non-aqueous sterile suspensions may include suspending agents and thickening agents. The formulations may be presented in unit-dose or multi-dose containers, for example sealed ampules and vials. Extemporaneous injection solutions and suspensions may be prepared from sterile powders, granules and tablets of the kind previously described.

In a specific embodiment, the drug product of the present invention is in the form of an injectable solution containing a predetermined amount (e.g., 25 mg) of the estrogenic composition in a sterile lyphilized cake which also contains lactose, sodium citrate, and simethicone. The pH of a solution containing the above ingredients may be adjusted using a suitable buffer (e.g., sodium hydroxide or hydrochloric acid). Reconstitution may be carried out according to known methods, e.g., using a sterile diluent (5 mL) containing 2 percent benzyl alcohol in sterile water. A preferred injectable solution is similar to Premarin® Intravenous made commercially available by Wyeth-Ayerst Laboratories.

The estrogenic composition also may be formulated such that it is suitable for topical administration (e.g., vaginal cream). These formulations may contain various excipients known to those skilled in the art. Suitable excipients may include, but are not limited to, cetyl esters wax, cetyl alcohol, white wax, glyceryl monostearate, propylene glycol, monostearate, methyl stearate, benzyl alcohol, sodium lauryl sulfate, glycerin, mineral oil, water, carbomer, ethyl alcohol, acrylate adhesives, polyisobutylene adhesives, and silicone adhesives.

In a preferred embodiment, the drug product is in the form of a vaginal cream containing the estrogenic composition as set forth herein present in a nonliquefying base. The nonliquefying base may contain various inactive ingredients such as, for example, cetyl esters wax, cetyl alcohol, white wax, glyceryl monostearate, propylene glycol, monostearate, methyl stearate, benzyl alcohol, sodium lauryl sulfate, glycerin, and mineral oil. Such composition may be formulated similar to Premarin® Vaginal Cream made commercially available by Wyeth-Ayerst Laboratories.

Dosage units for rectal administration may be prepared in the form of suppositories which may contain the estrogenic composition in a mixture with a neutral fat base, or they may be prepared in the form of gelatin-rectal capsules which contain the active substance in a mixture with a vegetable oil or paraffin oil.

In another aspect, the present invention relates to methods of treating mammals (e.g., man) in need of treatment for estrogen deprivation. These include the symptoms of hot flashes, dryness of the vagina, loss of bone mass, increased heart disease and the like. The methods include administering an effective amount of an estrogenic composition as defined herein to a mammal. The methods may be used for a number of treatments such as, but not limited to, vasomotor symptoms; atrophic vaginitis; osteoporosis; hypoestrogenism due to hypogonadism, castration, or primary ovarian failure; breast cancer in selected persons with metastatic disease; advanced androgen-dependent carcinoma of the prostate, abnormal uterine bleeding, and kraurosis vulvae. The administration may be cyclic, occurring for one or more short periods of time or courses of treatment (i.e. short-term use). Alternatively, the administration may be continuous, occurring over extended periods of time (i.e. long-term use). One example of long-term use would be from the onset of menopause until death. Cyclic and continuous administration may be either uninterrupted or interrupted. Uninterrupted administration occurs one or more times daily such that there is no break in treatment. Interrupted administration occurs other than daily, for example one or more times every other day.

In another aspect, the invention relates to a method of synthesizing an estrogenic composition. The method comprises subjecting an estrogenic composition comprising at least one estrogenic compound to thermal energy of high humidity that promotes the generation of at least one additional estrogenic compound in a final estrogenic composition that was not present in the initial estrogenic composition. The high humidity may be retained at 50% to 90% relative humidity. Additionally, the temperature during the synthesis step may be maintained between 30° to 60° C.

The present invention is explained in greater detail in the Examples that follow. These examples are intended as illustrative of the invention and are not to be taken are limiting thereof.

EXAMPLES

The present invention will now be described in greater detail with respect to the following numbered examples. In the examples, "mL" means milliliter, "° C." means degrees Celcius, "mM" means millimoles/liter, "M" means moles/liter, "Å" means angstrom, "$\mu$m" means micrometer, "nm" means nanometer, "mm" means millimeter, "mg" means milligram, and "m/z" means mass to charge ratio. These examples are for illustrating the invention and are not intended to limit the invention as set forth by the claims.

A list of instruments and equipment employed in the examples are as follows:
1. HPLC Chromatographic Procedures
   a. Analytical scale chromatographic system
      1. HP1100 Diode-array detector
      2. HP1100 Quaternary HPLC pump
      3. HP1100 Thermostatically controlled column compartment
2. Fraction Collection, Purification, and Crystallization
   a. ISCO Foxy Jr., Fraction Collector
   b. Büchi, Model R-124 rotary evaporator
3. Mass Spectral Analyses
   a. Liquid Chromatography (LC-MS)
      1. Instrument: Sciex Q-Star/Pulsar: quadrupole-tof
      2. Mode: Negative ionization
      3. Solvent: LC Matrix
   b. High Resolution Mass Spectrometer (HR-MS)
      1. Instrument: Sciex Q-Star/Pulsar: quadrupole-tof
      2. Sample input: Nanospray needle
      3. Solvent: Methanol
      4. Matrix: PEG 300 & PEG 400
B. Chemicals, Reagents, and Analytical Materials
   1. Chemicals and Reagents
      a. Acetonitrile (ACN), HPLC grade
      b. Methanol (MeOH), HPLC grade
      c. Milli-Q water
      d. Ammonium acetate, AR grade
      e. Glacial Acetic Acid, USP grade
      f. Nitrogen gas, zero grade

Example 1

Synthesis Utilizing $\Delta^{8,9}$-Dehydroestrone Sulfate 500 mg of $\Delta^{8,9}$-dehydroestrone sulfate is placed into a glass petri dish with the top loosely attached. This is then placed into a chamber set at 40° C. and 75% RH for 20 hrs. Upon removal the sample is chromotographed as given in Example 2. Individual components are then fraction collected and brought to dryness in a roto-evaporator.

Example 2

HPLC Chromatographic Separation with UV DAD Detection

An Agilent 1100 system consisting of a gradient pump, auto sampler, column heater, and UV DAD, was employed as the chromatographic system. Two mobile phases were employed in gradient mode as follows:

Mobile phase A containing 10 mM ammonium acetate and acetonitrile: water in a 12:88 ratio can be prepared as follows by combining 120 mL acetonitrile, 880 mL water and 10 mL 1 M ammonium acetate buffer. The ammonium acetate buffer may be prepared by dissolving approximately 7.7 mg of $NH_4$ acetate into 90 ml of water and adjusting the combination to a pH of 6.0 by adding in glacial acetic acid. The solution may then be transferred into a 100 mL flask and diluted with $H_2O$.

Mobile phase B containing 10 mM ammonium acetate and acetonitrile: water in a 60:40 ratio can be prepared as follows by combining 600 mL acetonitrile, 400 mL water and 10 mL 1M ammonium acetate buffer.

Figure 1A:
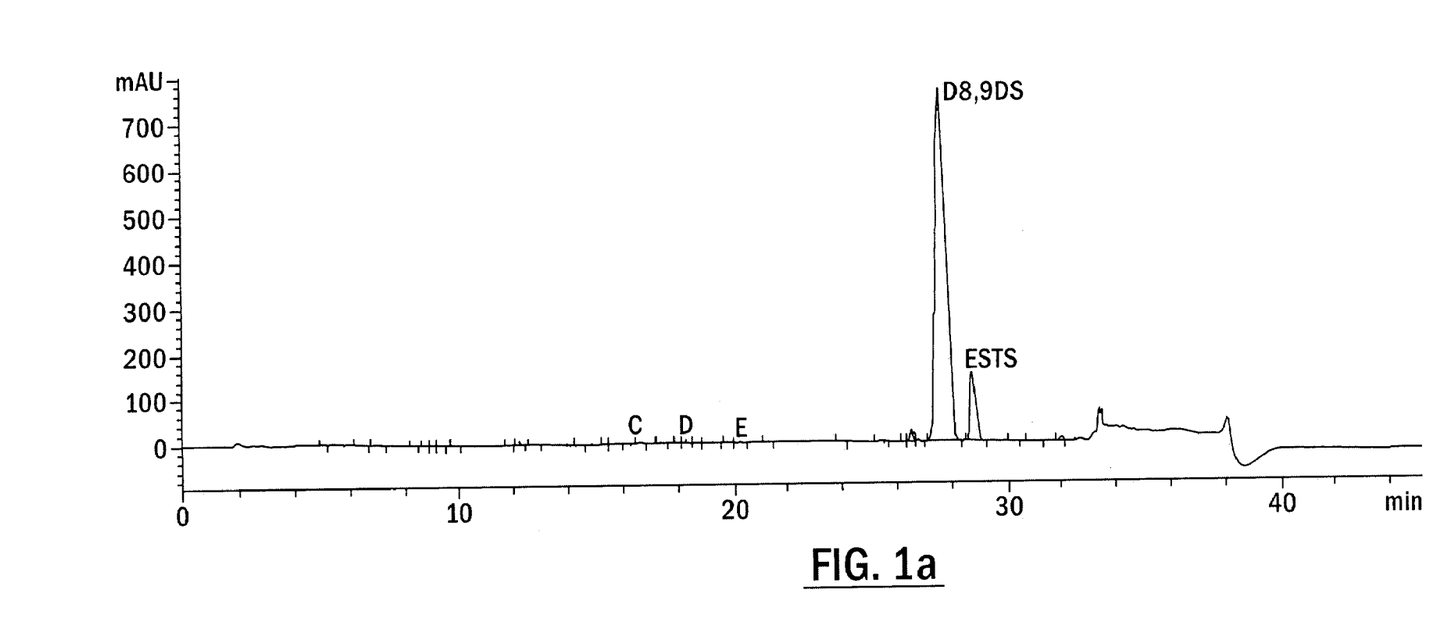
FIG. 1A illustrates a UV chromatogram of components C, E and $\Delta^{8,9}$-dehydroestrone sulfate.
Figure 1B:
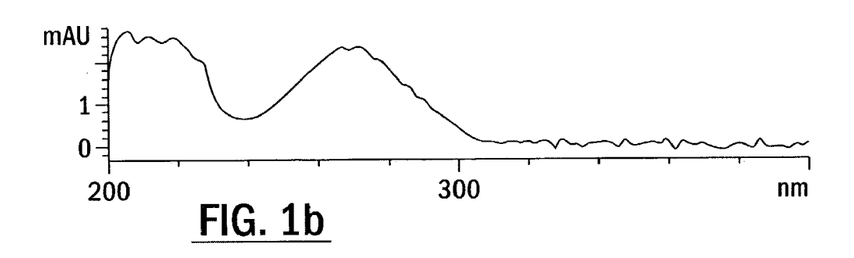
FIG. 1B illustrates the diode array UV spectrum of component C.
Figure 1C:
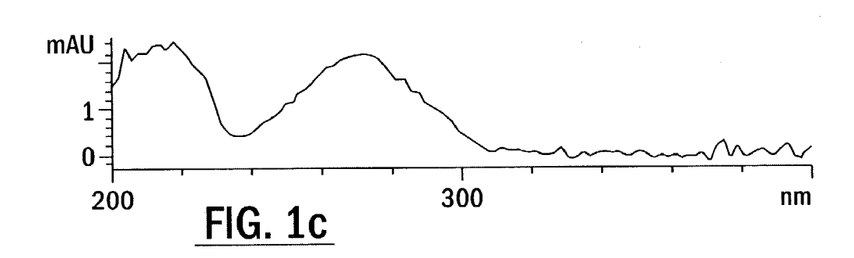
FIG. 1C illustrates the diode array UV spectrum of component E.
Figure 1D:
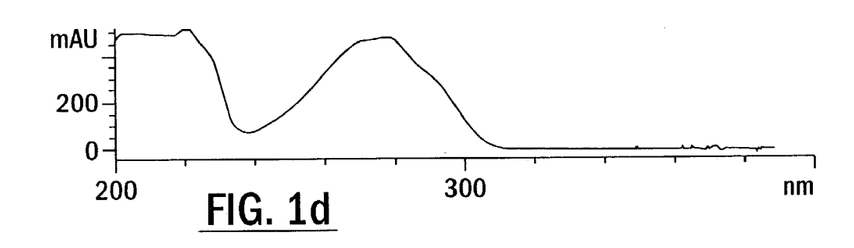
FIG. 1D illustrates the diode array UV spectrum of $\Delta^{8,9}$-dehydroestrone sulfate.
Figure 2:
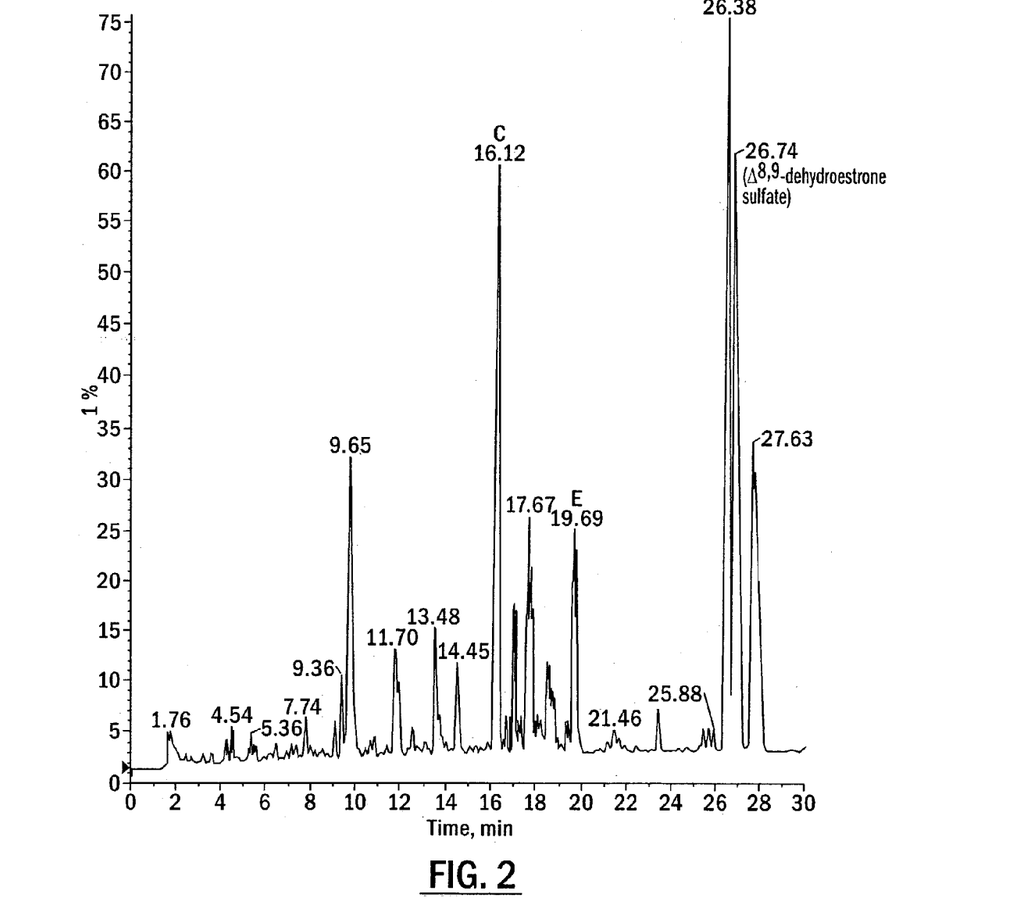
FIG. 2 depicts a UV chromatogram of a sample containing components C and E.

The gradient elution was performed by starting at 0% B and raising to 51% B in 30 minutes with a 0.83 ml/min flow rate. A YMC ODS-A $C_{18}$ 4.6×150 mm column was used at a temperature of 25° C. UV detection was performed using the DAD set to 220 nm and collecting UV spectral information from 200–400 nm. The sample is prepared buy dissolving a suitable amount of sample in mobile phase A and injecting a suitable volume. FIG. 1 illustrates a UV chromatogram and diode array UV spectra of components C and E and $\Delta^{8,9}$-dehydroestrone sulfate.

Example 3

HPLC Chromatographic Separation with MS Detection

An Agilent 1100 system consisting of a gradient pump, autosampler, column heater, and UV variable wavelength detector, was employed as the chromatographic system. MS detection is achieved using a Sciex Q-Star/Pulsar quadrupole time of flight mass spectrometer operating in the negative ion electrospray ionization mode.

Two mobile phases were employed in gradient mode as follows:

1) Mobile phase A containing 10 mM ammonium acetate and acetonitrile: water in a 12:88 ratio can be prepared as follows by combining 120 mL acetonitrile, 880 mL water and 10 mL 1M ammonium acetate buffer, as described in the previous example; and
2) Mobile phase B containing 10 mM ammonium acetate and acetonitrile: water in a 60:40 ratio can be prepared as follows by combining 600 mL acetonitrile, 400 mL water and 10 mL 1M ammonium acetate buffer.

Figure 3:
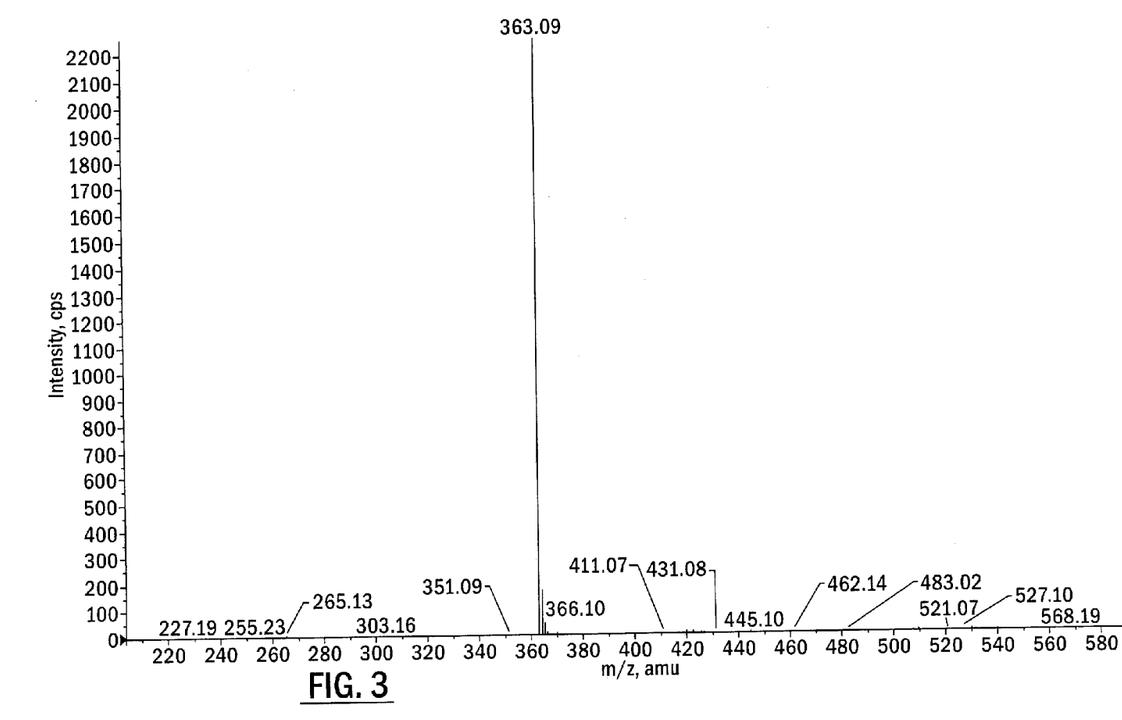
FIG. 3 illustrates a mass spectrum of component C.
Figure 4A:
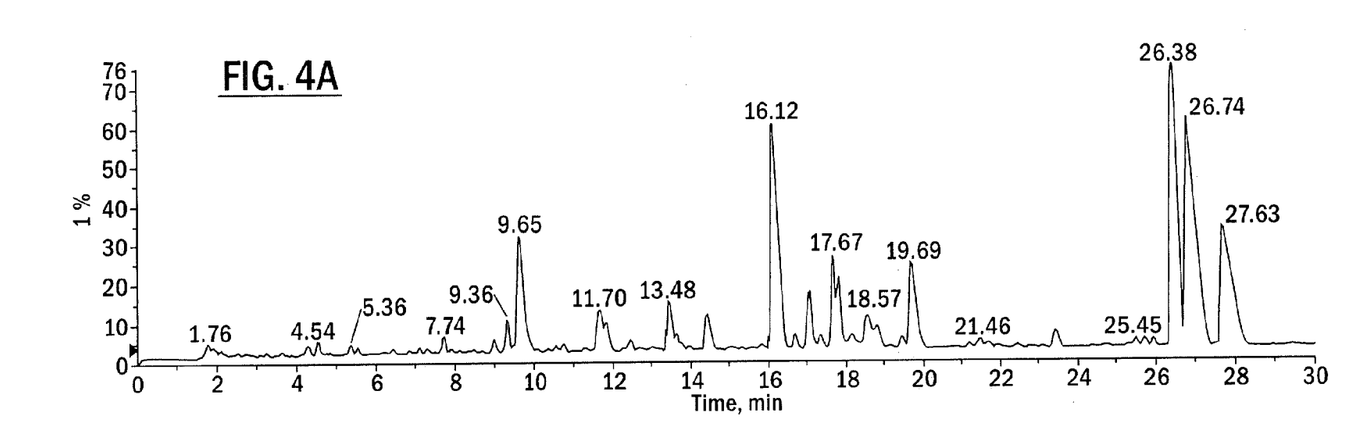
FIG. 4 depicts a single ion trace at m/z equal to 363 for the spectrum set forth in FIG. 3.
Figure 4B:
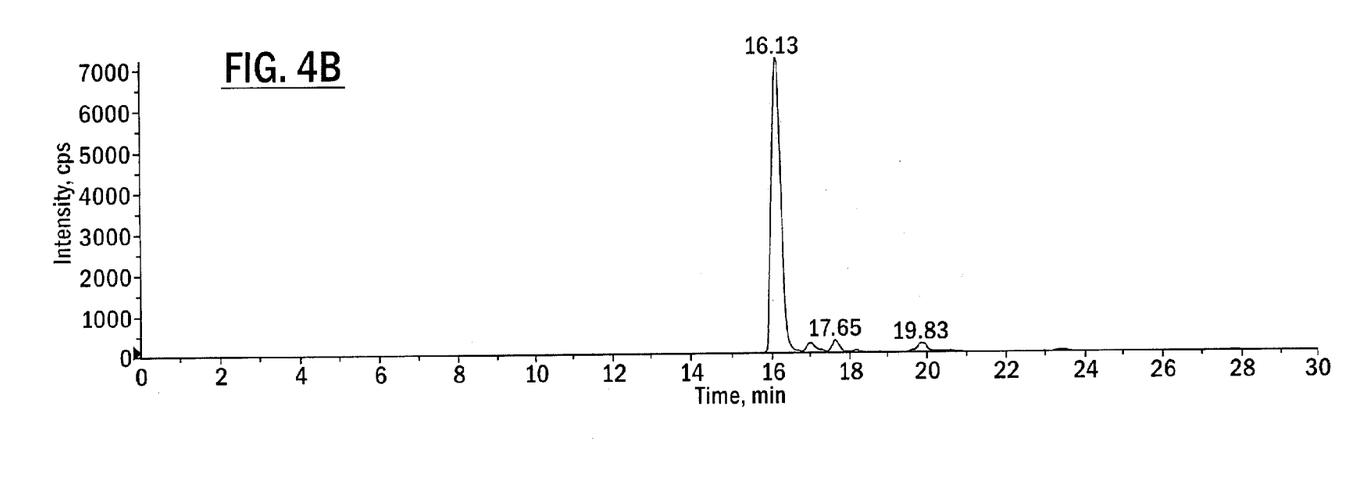
Figure 5:
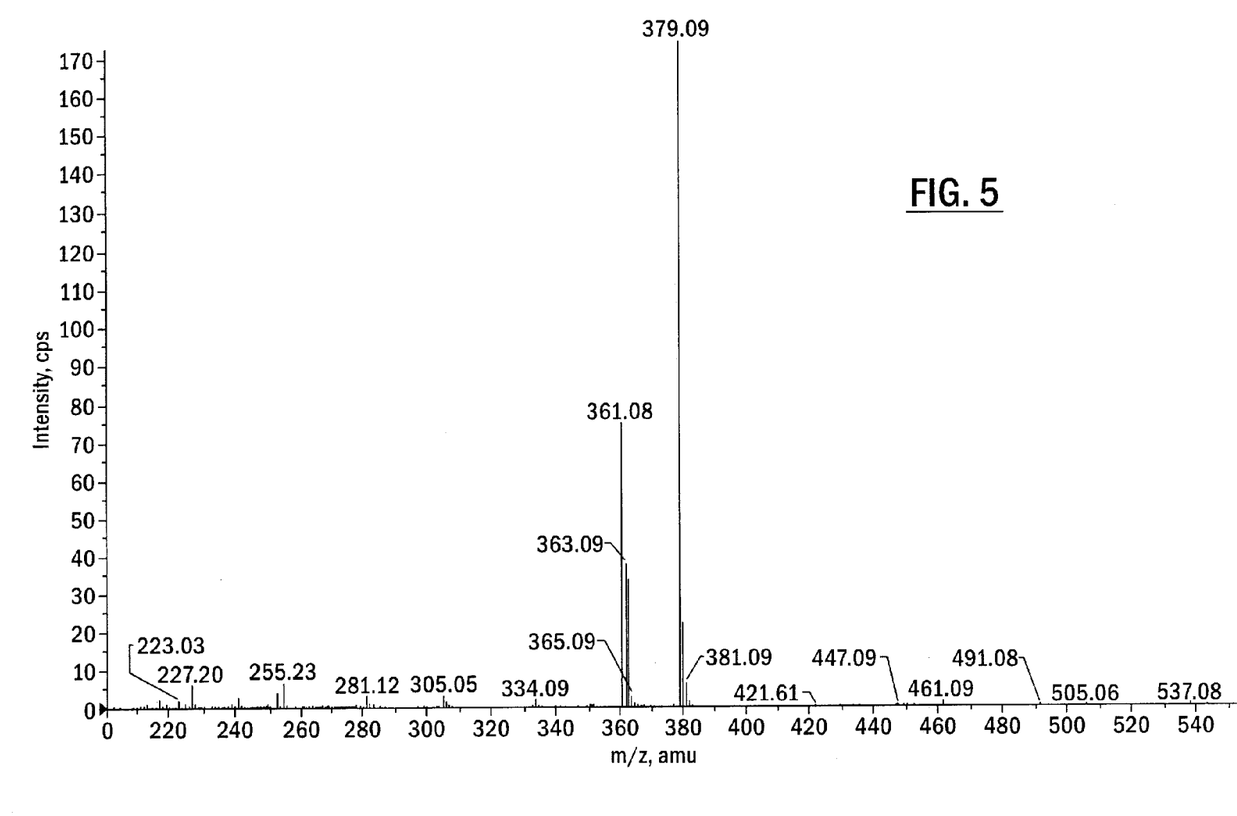
FIG. 5 depicts a mass spectrum of component E.
Figure 6A:
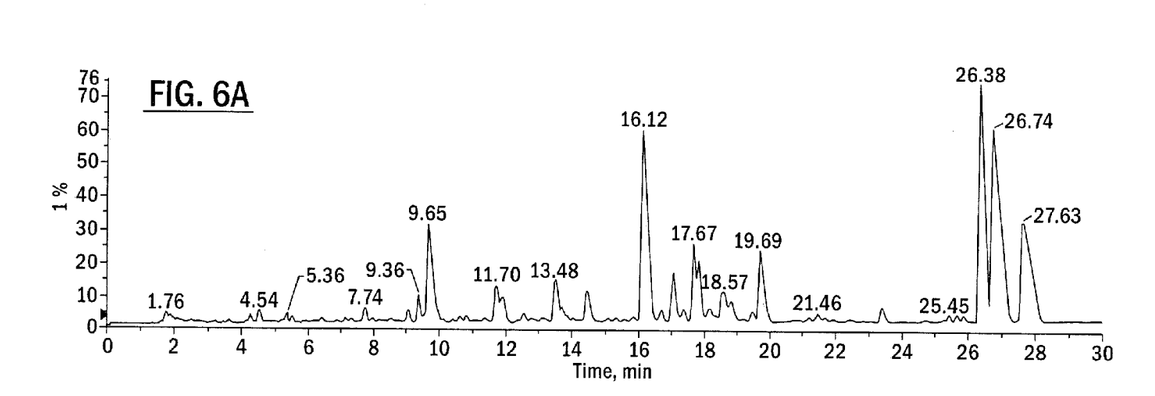
FIG. 6 illustrates a single ion trace at m/z equal to 379 for the spectrum set forth in FIG. 5.
Figure 6B:
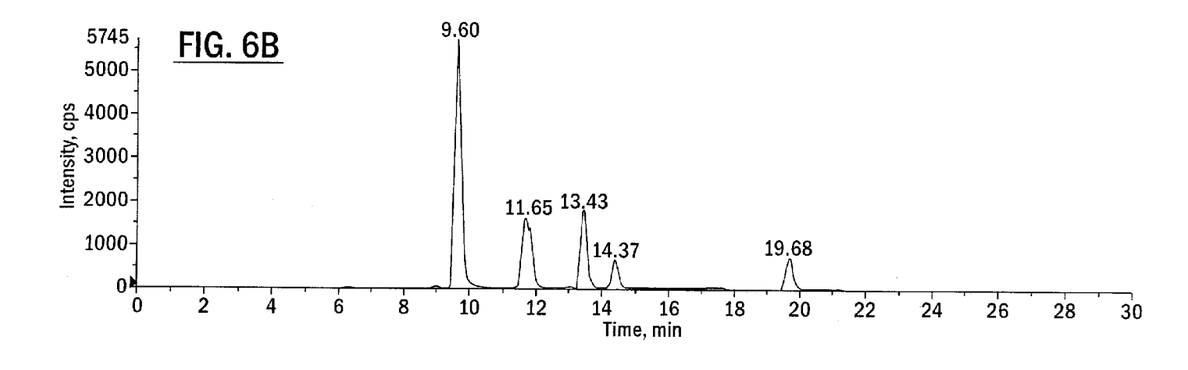

The gradient elution was performed by starting at 0% B and raising to 51% B in 30 minutes with a 0.83 ml/min flow rate. A YMC ODS-A $C_{18}$ 4.6×150 mm column was used at a temperature of 25° C. UV detection was performed using the variable wavelength detector set to 220 nm. The sample is prepared buy dissolving a suitable amount of sample in mobile phase A and injecting a suitable volume. FIG. 1 illustrates a UV chromatogram and FIGS. 3–6 illustrate MS spectra and single ion traces of components C and E. Fractions of components C and E where collected from the HPLC separation and dried under a stream of nitrogen. The fraction where then analyzed by HR ESI-MS to produce accurate masses, which were then used to predict the most probable empirical formulas.

| Component | accurate mass (amu) | EF |
|---|---|---|
| C | 363.0889 | $C_{18}H_{19}O_6S$ |
| E | 379.0851 | $C_{18}H_{19}O_7S$ |

The present invention has been described herein with reference to its preferred embodiments. These embodiments do not serve to limit the invention, but are set forth for illustrative purposes. The scope of the invention is defined by the claims that follow.

What is claimed is:

1. A compound comprising the formula wherein $R_1$ is selected from the group consisting of peroxy, hydroxy, halogen, ester, glucuronide, sulfate, phosphate, pyrophosphate and thiol, or a pharmaceutically acceptable salt thereof;
$R_2$ is selected from the group of glucuronide, sulfate, phosphate and pyrophosphate;
and $R_3$ is selected from the group consisting of hydroxy, ester, glucuronide, sulfate, phosphate and ketone.

2. The compound of claim 1, wherein said compound is:

or a pharmaceutically acceptable salt thereof.

3. The compound of claim 1, wherein said compound is:

or a pharmaceutically acceptable salt thereof.

4. A method of treating a subject for estrogen deprivation comprising administering a compound comprising the formula:

wherein $R_1$ is selected from the group consisting of peroxy, hydroxy, halogen, and thiol, or a pharmaceutically acceptable salt thereof; and $R_2$ is selected from the group consisting of hydroxy, ester, glucoronide, sulfate, phosphate and ketone.

5. The method according to claim 4, wherein said compound is 14-hydroxy-$\Delta^{8,9}$-Dehydroestrone Sodium Sulfate.

6. The method according to claim 4, wherein said compound is 14-hydroperoxy-$\Delta^{8,9}$-Dehydroestrone Sodium Sulfate.

7. A method of synthesizing an estrogenic composition, said method comprising:

subjecting an estrogenic composition comprising at least one estrogenic compound to thermal energy and high humidity that promotes the generation of at least one additional estrogenic compound in a final estrogenic composition that was not present in the initial estrogenic composition.

8. The method according to claim 7, wherein the composition is maintained at a temperature between 30° to 60° C.

9. The method according to claim 7, wherein the composition is kept at 50% to 90% relative humidity.

10. The method according to claim 7, wherein said subjecting step is carried out from about 3 to about 72 hours.

11. The method according to claim 7, wherein the estrogenic composition comprises a conjugated estrogen selected from the group consisting of a sulfate of an estrogen, a glucuronide of an estrogen, and mixtures thereof.

12. The method according to claim 7, wherein the estrogen is selected from the group consisting of estrone, 17α-estradiol, 17β-estradiol, equilin, 17α-dihydroequilin, 17β-dihydroequilin, equilenin, 17α-dihydroequilenin, 17β-dihydroequilenin, $\Delta^{8,9}$-dehydroestrone, 17α-$\Delta^{8,9}$-dehydroestradiol, 17β-$\Delta^{8,9}$-dehydroestradiol, ethinyl estradiol, estradiol valerate, 6-OH equilenin, 6-OH 17α-dihydroequilenin, 6-OH 17β-dihydroequilenin, 17-β hydroxy derivatives thereof, salts thereof, ketones thereof, and mixtures thereof.

13. The method according to claim 7, wherein the estrogenic composition comprises $\Delta^{8,9}$-dehydroestrone sulfate.

* * * * *

UNITED STATES PATENT AND TRADEMARK OFFICE
CERTIFICATE OF CORRECTION

PATENT NO. : 6,992,075 B2
DATED : January 31, 2006
INVENTOR(S) : Hill et al.

Page 1 of 1

It is certified that error appears in the above-identified patent and that said Letters Patent is hereby corrected as shown below:

Column 11,
Line 34, should read -- ester, glucuronide, sulfate, phosphate and ketone. --.

Column 12,
Line 20, should read -- glucuronide, sulfate, phosphate and ketone. --.

Signed and Sealed this

Thirtieth Day of May, 2006

JON W. DUDAS
*Director of the United States Patent and Trademark Office*